US005521285A

United States Patent [19]
Pomato et al.

[11] Patent Number: 5,521,285
[45] Date of Patent: May 28, 1996

[54] CTAA 28A32, THE ANTIGEN RECOGNIZED BY MCA 28A32

[75] Inventors: Nicholas Pomato, Silver Spring, Md.; Ebo S. Bos, Oss, Netherlands; Janet H. Ransom, Shepherdstown, W. Va.; Michael G. Hanna, Jr., Frederick, Md.

[73] Assignee: Akzo Nobel N.V., Arnhem, Netherlands

[21] Appl. No.: 41,529

[22] Filed: Apr. 1, 1993

Related U.S. Application Data

[63] Continuation of Ser. No. 508,373, Apr. 12, 1990, abandoned, which is a continuation-in-part of Ser. No. 38,811, Apr. 15, 1987, Pat. No. 4,997,762, which is a continuation-in-part of Ser. No. 697,078, Jan. 31, 1985, Pat. No. 4,828,991, which is a continuation-in-part of Ser. No. 575,533, Jan. 31, 1984, abandoned.

[51] Int. Cl.$^6$ .......................... A61K 39/00; A61K 35/14; C12Q 1/00; G01N 33/53; C12N 5/00; C07K 1/00; C07K 14/00; C07K 16/00; C07K 16/28; C07K 16/30; C07K 17/00

[52] U.S. Cl. .................. 530/350; 424/184.1; 435/7.23; 435/240.26; 530/388.1; 530/388.22; 530/388.8; 530/388.85; 530/828

[58] Field of Search .................................. 424/88, 184.1; 435/7.23, 240.26; 514/2; 530/388.1, 388.22, 388.8, 388.85, 828, 350

[56] References Cited

U.S. PATENT DOCUMENTS

| 4,727,021 | 2/1988 | Cote et al. | 436/548 |
|---|---|---|---|
| 4,828,991 | 5/1989 | Hanna et al. | 435/68 |
| 4,997,762 | 3/1991 | Hanna, Jr. et al. | 435/240.27 |

FOREIGN PATENT DOCUMENTS 0199586  10/1986  European Pat. Off.

OTHER PUBLICATIONS

Goldenberg et al (1976) "Antigens Associated with . . . " Cancer Res 36: 3455–3463.
Kohler et al., Nature, No. 256:495–497 (1975).
Haspel et al., Cancer Research, 45:3951–3961 (1985).
Biological Abstracts, vol. 89, No. 6, issued Mar. 15, 1990, Kitamura, K., "A New Colorectal Carcinoma Associated Antigen Recognized by Murine Monoclonal Antibody A7", Abstract No. 60871, J. Kyoto Perfect Univ Med, 1989, 98(12), 1259–1268 (Eng.).
Biological Abstracts, vol. 86, No. 7, issued Oct. 1, 1988, R. P. McCabe et al., "Preclinical Studies on the Pharmokinetic Properties of Human Monoclonal Antibodies to Colorectal Cancer and Their Use for Detection of Tumors", Abstract No. 71598, Cancer Res, 1988, 48(15), 4348–4353 (Eng.).
Biological Abstracts, vol. 87, No. 12, issued 1989, K. Kitamura et al., "Immunochemical Characterization of the Antigen Recognized by the Murine Monoclonal Antibody A7 Against Human Colorectal Cancer", Abstract No. 128049, Tohokv J. Exp Med, 157(2), 83–94 (Eng.).
Biological Abstracts, vol. 91, issued 1991, Y. Chimori et al, "Identification and Characterization of a Colon Cancer-associated Antigen Expressed on Leukemia–lymphoma Cell Lines", Abstract No. 97740, Int. J Cancer, 1991, 47(3), 426–430 (Eng).

Biochemical and Biophysical Research Communications, vol. 128, No. 1, issued Apr. 16, 1985, (Washington DC, USA), Hollmann et al., "Monoclonal Antibody-defined Circulating Human Tumor-associated Antigen with Epitope Shared by Cytokeratin", pp. 34–39.
The Journal of Immunology, vol. 137, No. 5, issued Sep. 1, 1986 (Washington DC USA), Raychaudhuri et al., "Tumor--specific Idiotype Vaccines. I. Generation and Characterization of Internal Image Tumor Antigens", pp. 1743–1749.
Science, vol. 228, issued Apr. 12, 1985 (Washington DC, USA), Marx, "Making Antibodies Without the Antigens", pp. 162–165.
Cancer Research, vol. 44, No. 12, issued Dec. 1984 (USA), Schmidt et al., "Characterization of Monoclonal Antibodies to Novikoff Hepatoma Cytokeratin Antigen p39", pp. 5867–5879.
Journal of Cellular Biochemistry, vol. 24, issued 1984 (Los Angeles, CA, USA) Franklin et al., "A Monoclonal Antibody Recognizes an Epitope Common to an Avian-specific Nuclear Antigen and to Cytokeratins", pp. 1–14.
Cancer Research, vol. 45, No. 11, issued Nov. 1985, (Bethesda, MD, USA), Koprowska et al., "Common Antigenic Sites on Exfoliated Cells Derived from Cervical Carcinoma and in Tumor Cells of Nonuterine Origin as Demonstrated by Monoclonal Antibodies in Immunoperoxidase Assay", pp. 5964–5968.
Goligher, J. C., Surgery of the Anus, Rectum and Colon, 4th ed., London: Baillere Tindall (1980) 47–471.
Gold, P. and Freedman, S. O., J. Exp. Med. (1965) 122:467–481.
Yeoman, L. C. et al., Human Colon Tumor Antigens. In: H. Busch and L. C. Yeoman (eds.), vol. 19, 231–271, New York: Academic Press, Inc. (1982).
Magnani, J. L. et al., Cancer Res. (1983) 43:5489–5492.
Artigas, C. et al., Cancer Res.(1986) 45:1874–1881.
Silverberg, E., CA (1983) 33:9–25.
Hoover, H. C., Jr. et al. Biologic Therapy of Cancer Principles and Practices. (1990) In press. J. P. Lippincott Co.
Hoover, H. C., Jr., et al. Cancer (1985) 55:1236–1243.
Blasczyk, M. et al., Cancer Res. (1984) 44:245–253.
Ross, A. H., et al., Biochem. Biophys. Res. Comm. (1986) 135:297–303.

Primary Examiner—Christine M. Nucker
Assistant Examiner—Nita M. Minnifield
Attorney, Agent, or Firm—William M. Blackstone; Mary E. Gormley

[57] ABSTRACT

The present invention comprises the epitope recognized by the human monoclonal antibody 28A32, the human tumor antigen containing this epitope, which we have identified, isolated and characterized, and human MCA 28A32. The invention also relates to the use of antibodies to the antigen containing this epitope for diagnosis and monitoring of treatment of cancer and to the use of this antigen in the preparation of vaccines to elicit an immune response similar to that obtained against tumor cells containing this epitope.

5 Claims, 8 Drawing Sheets

CTAA ✦ 28A32-50K

CTAA ✦ 28A32-46K

| | 1<br>ᵃX | Q | H | K | I | T | V | Q | S | 10<br>I |
|---|---|---|---|---|---|---|---|---|---|---|
| | K | N | D | I | N | S | F | D | Q | 20<br>X |
| | G | V | E | L | G | K | Q | L | A | 30<br>K |

46K

| | 1<br>X | V | A | K | N | K | F | F | R | 10<br>S |
|---|---|---|---|---|---|---|---|---|---|---|
| | T | N | Y | D | L | G | F | K | S | P |

36K

| | 1<br>X | E | P | D | S | A | Q | P | P | 10<br>V |
|---|---|---|---|---|---|---|---|---|---|---|
| | Q | Y | Y | T | N | F | D | Y | T | 20<br>N |
| | F | A | T | N | I | X | T | L | | |

32K

| | 1<br>X | L | Y | ᵇT<br>(Q) | F<br>(D) | N<br>(E) | A | M | F | 10<br>I |
|---|---|---|---|---|---|---|---|---|---|---|
| | A | V<br>(Q) | X | X | X | K | A<br>(N) | M | | |

ᵃX  Indicates that an amino acid could not be identified at this position.

ᵇ( ) Indicates that this amino acid has an equal probability of occupying the position indicated.

CTAA 28A32, THE ANTIGEN RECOGNIZED BY MCA 28A32

This is a continuation of application Ser. No. 07/508,373 filed Apr. 12, 1990, now abandoned, which is a continuation-in-part of U.S. Ser. No. 07/038,811, filed Apr. 15, 1987 and issued as U.S. Pat. No. 4,997,762 on Mar. 5, 1991, which is a divisional application of U.S. Ser. No. 06/697,078, filed Jan. 31, 1985 and issued as U.S. Pat. No. 4,828,991 on May 9, 1989, which is a continuation-in-part of U.S. Ser. No. 06/575,533 filed Jan. 31, 1984, now abandoned.

BACKGROUND OF THE INVENTION

Colorectal caner is the second most prevalent cancer in the United States, affecting both men and women. Until recently, the only viable treatment for this disease has been surgery, which has a poor prognosis for patients with transmural extension of tumor and metastasis to regional lymph nodes. A dramatically improved prognosis was indicated in a recently reported randomized Phase II-active specific immunotherapy trial, which showed that immunization of patients with autologous tumor cells admixed with Tice BCG (Bacillus Calmette Guerin) (Institute for Tuberculosis Research, Chicago, Ill.) significantly increased delayed cutaneous hypersensitivity responses and, over a four year period of time, significantly decreased recurrence and mortality (3).

There have been numerous publications describing the identification of colon carcinoma-associated antigens (4–9). The majority of these antigens were identified using monoclonal antibodies generated by immunizing mice with some form of the colon tumor (extracts, dissociated cells, membrane preparations, and etc.) or colon tumor cell lines. These mouse antibodies identify a repertoire of antigens that were antigenic in the mouse. In addition to these studies, there are several reports of human monoclonal antibodies that show specific reactivity with tumor material.

Using peripheral blood B-cells from colorectal patients actively immunized with autologous tumor cells and BCG in immunotherapy protocols, we have successfully developed a strategy for producing human anti-tumor monoclonal antibodies (11). Unlike mouse monoclonal antibodies generated against human colon cancer, which often recognize tissue components also found in healthy individuals, such as CEA, blood group determinants or histocompatibility antigens, indicating that these antibodies are characterized by a specificity confined to those epitopes that are recognized as immunogenic in the autologous host.

We have used these human monoclonal antibodies as probes to identify tumor antigens. We have identified a particular antigen in colon tumors, extracts of colon tumor cell lines and human tumor xenografts generated in nude mice. The subject antigen is characterized by containing an epitope recognized by human monoclonal antibody (MCA) 28A32, which has been detected in approximately 70% of all colorectal tumors.

SUMMARY OF THE INVENTION

The present invention comprises the epitope recognized by the human monoclonal antibody 28A32 and the human tumor antigen, designated CTAA 28A32, containing this epitope, which we have identified, isolated and characterized. The cell line for producing human monoclonal antibody 28A32 is claimed in U.S. Pat. No. 4,997,762 issued Mar. 5, 1991. The invention also relates to the use of antibodies to the antigen containing this epitope for diagnosis and monitoring of treatment of cancer and to the use of this antigen in the preparation of vaccines to elicit an immune response similar to that obtained against tumor cells containing this epitope.

BRIEF DESCRIPTION OF THE DRAWINGS

The purity of the antigen is demonstrated in FIG. 5 and FIGS. 6a and 6b by SDS polyacrylamide gel electrophoresis and HPLC, respectively.

DESCRIPTION OF THE PREFERRED EMBODIMENTS

We have found antigen containing the epitope recognized by human MCA 28A32 in approximately 70% of the colon tumors examined (11). We have also found the colon carcinoma cell lines HT-29, SW1463, SW948, SW403, LS174, LoVo and WiDr (ATCC, Rockville, Md.) to contain the same antigen. Because of the low reactivity of human MCA 28A32 with matched normal colonic tissue, it is evident that this antigen is preferentially expressed in colon tumor cells.

Purification of the antigen was achieved by salt precipitation, gel filtration chromatography, ion exchange chromatography, and hydrophobic interaction chromatography. Each purified component of CTAA 28A32 migrated as a single protein by denaturing gradient polyacrylamide gel electrophoresis under reducing conditions.

The molecular weights of the native proteins characteristic of the antigen, as estimated by gel filtration chromatography, were the same as that obtained by SDS-PAGE. These are approximately 50K, 46K, 36K and 32K for the four antigenic proteins recognized by MCA 28A32.

Based on crude fractionation of cellular components, it has been determined that the 36K protein can be found associated with membranes and the 50K, 46K and 32K proteins are found in the cytoplasm of cells.

Partial protein sequence information has been obtained for all of the proteins of CTAA 28A32. Based on computer searches of the NBRF Protein Database, no homologies have been found for the 50K, 36K and 32K proteins. The 46K protein shows a strong homology with human α-enolase but has some amino acid sequences that differ, indicating that this is a unique protein that could represent an altered form of this enzyme.

We have isolated this tumor associated antigen by its reactivity with the 28A32 human monoclonal antibody. Based on the presence of this antigen in various colon carcinoma, as well as its ability to stimulate cloned T-cells, it is a significant antigen for diagnostic purposes and for vaccine development. CTAA 28A32 is defined and clearly identified by its immunoreactivity with human MCA 28A32, its molecular weight characterization and the partial protein sequence information.

Extraction and Purification of CTAA 28A32 Recognized by Human MCA 28A32

Reactivity of MCA 28A32 antibody was assessed with seven human colon tumor cell lines, enzymatically dissociated cells from eight primary colon tumors, and enzymatically dissociated tumor cells from four colon tumor xenografts, all prepared as air-dried cytospin preparations. For the seven colon tumor cell lines, the human IgM monoclonal antibody 28A32 was used at a concentration of 300 nanograms per slide. The antibody was tested on the eight primary tumor cell preparations as well as the colon tumor xenograft preparations. Formalin-fixed, paraffin embedded colon tumor tissues and the corresponding normal colon from three patients were also tested using the indirect procedure.

Cell Lines

Human colon adenocarcinoma cell lines HT-29, SW-1463, SW-948, SW-403, Ls-174, LoVo and WiDr were obtained from the American Type Culture Collection (Rockville, Md.). The cells were cultured in recommended culture media supplemented with 10% fetal bovine serum (FBS). All cells were incubated at 37° C. and in an atmosphere of 5% $CO_2$.

Monoclonal Antibodies

The heterohybridoma cell line producing the human monoclonal antibody MCA 28A32 was grown in hollow fiber cartridges in the presence of RPMI 1640 supplemented with FBS. The antibody, a human immunoglobulin-M (IgM), was purified by gel filtration and ion exchange chromatography.

Indirect Immunohistochemistry with MCA 28A32

Biotin labeling of MCA 28A32 and control human IgM was performed in physiological buffer with biotin —N— hydroxysuccinimde (Calbiochem) dissolved in dimethylformamide at a initial molar ratio of 120:1 biotin to antibody. After 15 minutes at room temperature, the reaction mixture was dialyzed against PBS in order to remove the free biotin. The biotinylated antibody was reacted with formalin-fixed paraffin embedded colon tumors and the non-involved normal colon taken from the margin of the resected colon at surgery. The ABC peroxidase method (Vector Laboratories) was used for visualization of the reactivity. The antibody was titered at various concentrations up to 40 µg/ml of antibody.

Reactivity of the biotinylated antibody was also examined against other normal tissues. Formalin-fixed paraffin embedded sections of normal tissues from breast, esophagus, stomach, gall bladder, kidney, and lung were used to ascertain the specificity of this antibody.

All seven colon tumor cell lines were reactive with 28A32 using the indirect peroxidase method. The antibody was also reactive with seven of eight primary colon tumors as well as all four xenograft preparations. This data is summarized in Table 1.

MCA 28A32 directly labelled with biotin was reacted with seven pairs of formalin-fixed, paraffin embedded colon tumor and autologous non-involved colon. Results obtained from these various tissue sections can be seen in Table 2. Good specificity was seen with tumor tissue versus normal colon at both the highest concentration used (40 µg/ml) and at lower concentrations of antibody.

The biotinylated antibody MCA 28A32 was also tested on a variety of formalin-fixed, paraffin embedded normal tissues. The granulocytes, ductle tissue, and all portions of normal breast tissue from two individuals were negative. For normal esophagus, one individual showed moderate to strong staining of normal epithelium at the highest antibody concentration tested (80 µg/ml) and produced reduced staining at lower concentrations. In the second patient, no staining of the esophagus was seen at a concentration of 40 µg/ml antibody and weak staining was observed at a higher concentration of 80 µg/ml. In normal stomach, two patients showed no staining. In the gall bladder, there was weak staining of the epithelium. In kidney, the epithelium of collecting tubules reacted with the antibody, but no reactivity with glomeruli was seen. In the liver, weak staining of the epithelium of tubules and ducts was seen, but no staining of the parenchyma was noted. In the lungs, no staining of the bronchial epithelium or of the alveoli was seen. This data is summarized in Table 3.

Antigen Extraction

HT-29 or WiDr cells were harvested by treatment with 1.0 mM ethylenediame tetraacetic acid (EDTA) and phosphate buffered saline (PBS). After pelleting the cells the supernatant fluid, designated as cell wash, was saved separately from the cells. For the 50K and 46K proteins of CTAA 28A32, the cell washes were found to contain as much of these antigens as are present from the cells themselves. Cell wash material for these antigens had fewer contaminants than extracts from the intact cells, thus providing a good source of material for the isolation of these two proteins. The 36K and 32K proteins of CTAA 28A32 were obtained from extracts of frozen cells, which were generated by treatment of the cells with a lysis buffer consisting of 50 mM Tris, pH 7.5, 150 mM NaCl, 5.0 mM EDTA, 1.0 mM phenylmethylsulfonyl fluoride and 0.5% Nonidet P-40.

The cells were stirred at 4° C. for 60 minutes and then clarified by ultracentrifugation at 100,000×g for 30 minutes. Cell wash material was also clarified by this procedure.

Salt Precipitation of CTAA 28A32

The clarified supernatant fluid from extracted cells or cell wash material was maintained at 4° C. and made to 30% saturation by the addition of solid ammonium sulfate. The mixture was stirred at 4° C. for at least 60 minutes and then centrifuged at 40,000×g for 30 minutes. The supernatant fluid was then removed and made up to 80% saturation by the addition of solid ammonium sulfate, stirred at 4° C. for at least 60 minutes, and then centrifuged again at 40,000×g for 30 minutes.

The ammonium sulfate pellet from the cell wash containing the 50K and 46K proteins was dissolved in a small volume of PBS, and the pellet from the lysed cells containing the 36K and 32K proteins was dissolved in a small volume of 50 mM Tris, pH 8.0.

Gel Filtration Chromatography

The CTAA 28A32 proteins were chromatographed on a Sephacryl S-200 (5.0 by 90 cm) column pre-equilibrated in PBS at a flow rate of 1.5 ml/min. Extracts were analyzed by SDS-PAGE and Western blot analysis and appropriate peaks were pooled for further processing.

Purification of CTAA 28A32

Figure 1:
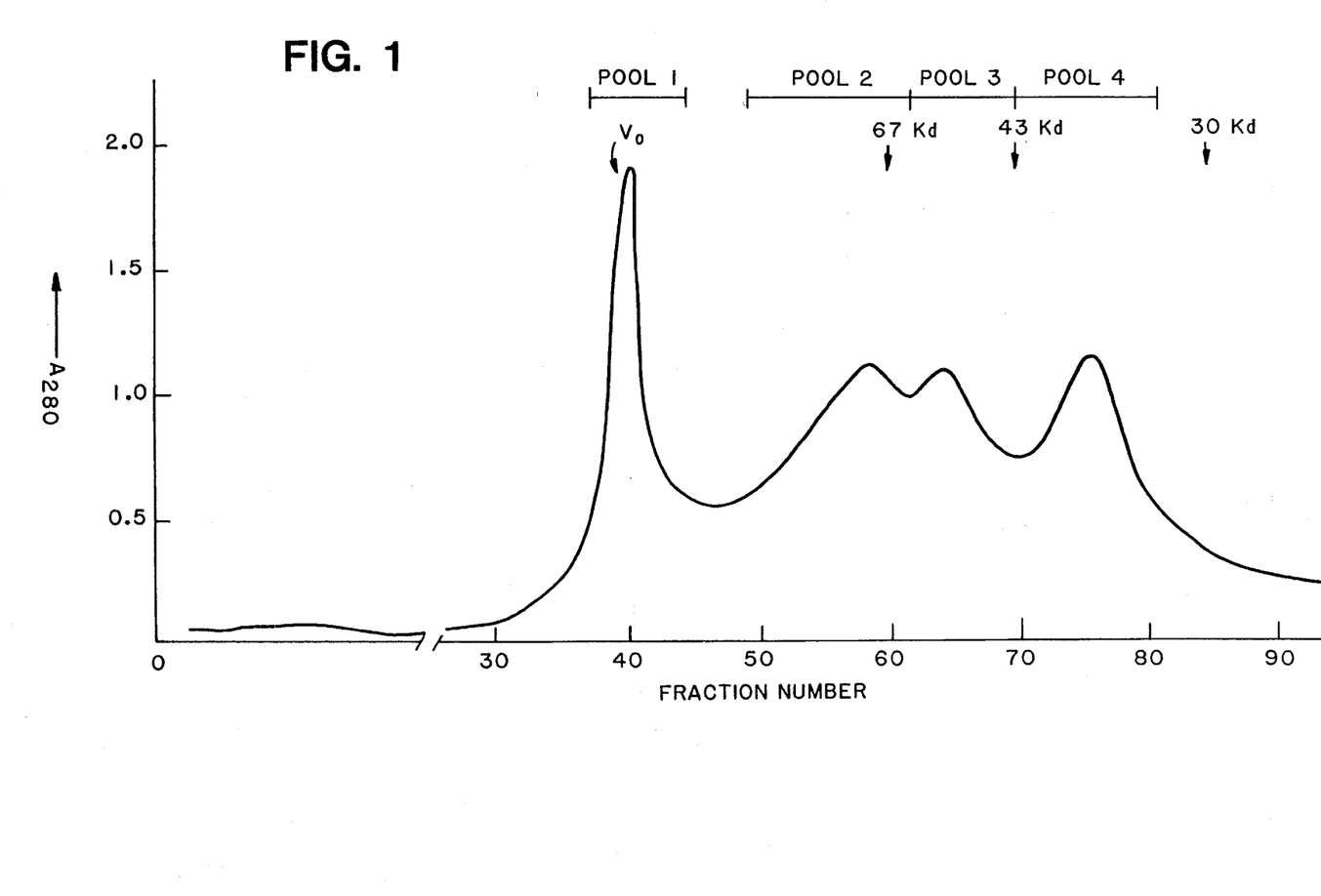
FIG. 1 illustrates gel filtration chromatography of CTAA 28A32.

Since the 50% and 46K proteins of CTAA 28A32 are enriched in the cell washes, and the 36K and 32K proteins are enriched in cell lysates, both of these sources were used for the generation of purified antigens. When both preparations of antigens were chromatographed by gel filtration after ammonium sulfate precipitation, an identical chromatographic pattern was observed. As illustrated in FIG. 1, several peaks were obtained after chromatography. For the 50K and 46K proteins, pools 2 and 3 were combined for further processing. For the 36K and 32K proteins, pool 4 was used for further purification. As FIG. 1 illustrates, good resolution according to molecular size was obtained on the Sephacryl S-200 column and good purification of the antigen was achieved by this step.

Ion Exchange Chromatography

Figure 2:
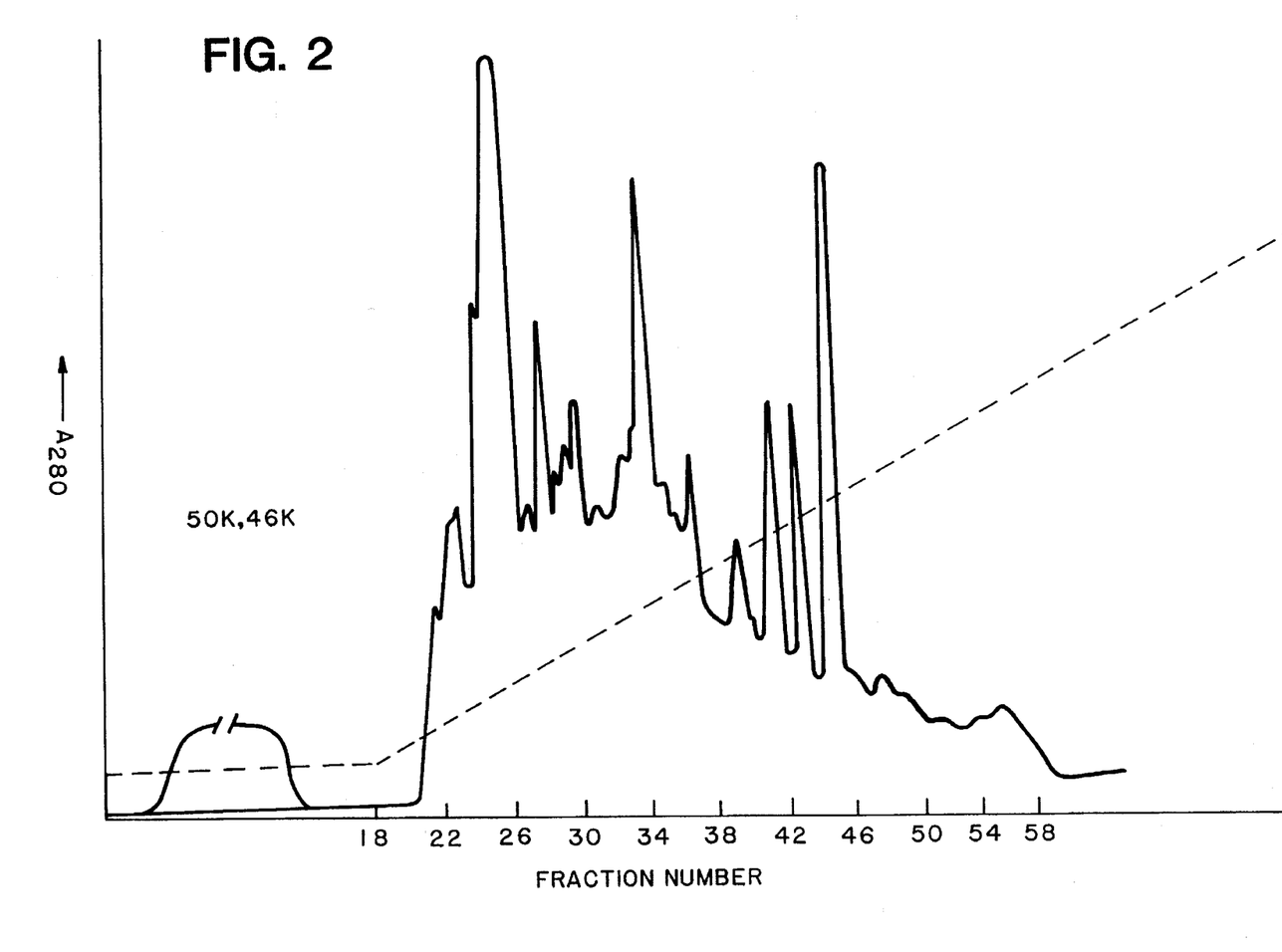
FIG. 2 shows anion exchange chromatography of the 50K and 46K fractions, pools 2 and 3, after gel filtration chromatography of this antigen.

The pool containing the 50K and 46K proteins from the Sephacryl S-200 column was dialyzed against buffer containing 20 mM Tris/HCl, pH 7.4. This pool was loaded onto a Mono Q column (Pharmacia, Inc.) previously equilibrated in the same buffer. As illustrated in FIG. 2, under the conditions used the flow through material from this column contained the 50K and 46K proteins. The majority of the protein was bound to the column and was eluted with a linear salt grade.

Figure 3:
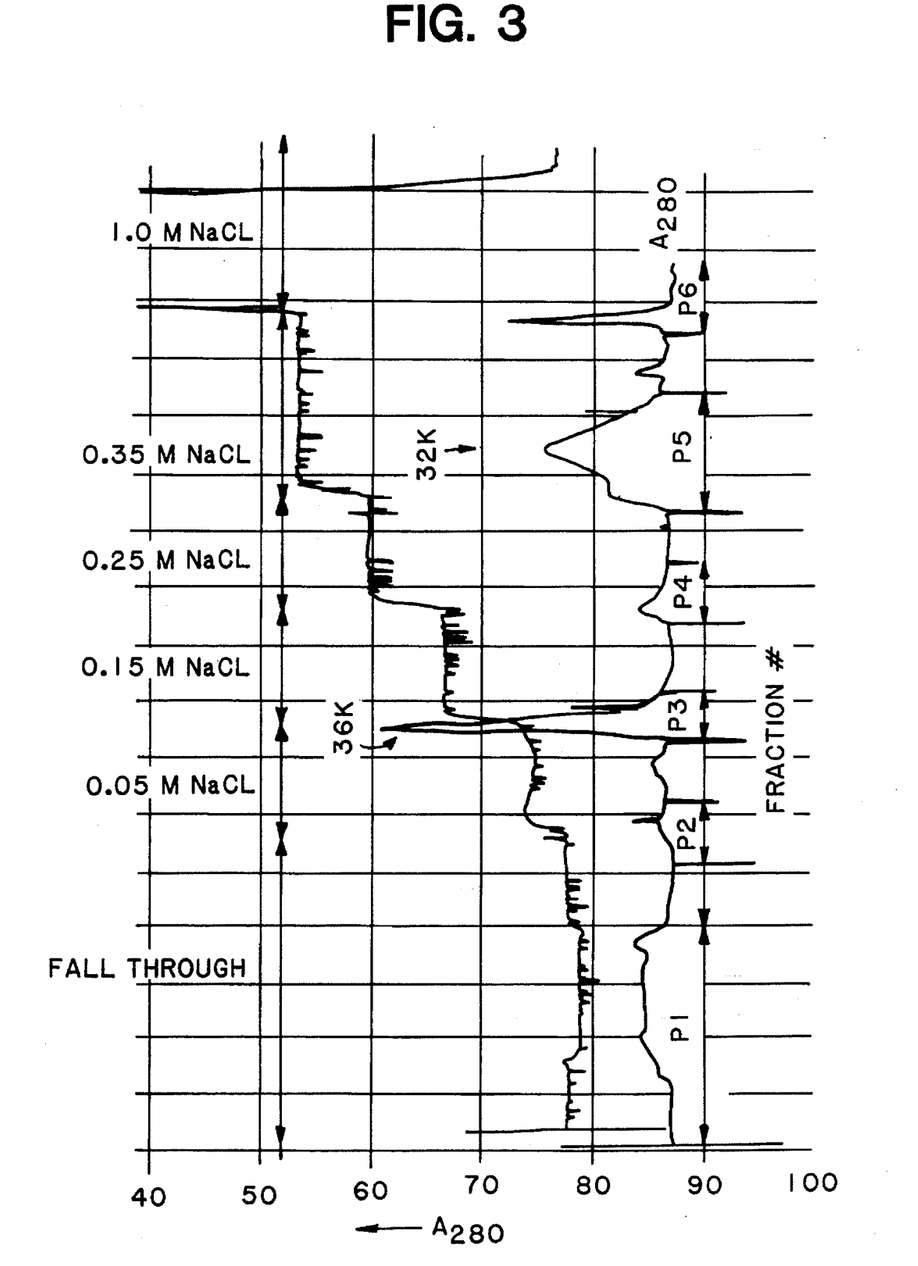
FIG. 3 illustrates cation exchange chromatography of the 36K and 32K antigens from pool 4 of FIG. 1.

Pool 4 of the S-200 column (derived from the cell extract material) was dialyzed against 50 mM sodium acetate buffer, pH 5.5, and loaded onto a S-Sepharose cation exchange column (Pharmacia, Inc.), previously equilibrated in the same buffer. The column was eluted by increasing the sodium chloride concentration of the acetate buffer by 0.05M acetate buffer. As shown in FIG. 3, pool 3 contained the 36K protein and pool 5 contained the 32K protein of CTAA 28A32 determined by SDS-PAGE and western blot analysis.

Hydrophobic Chromatography

Figure 4:
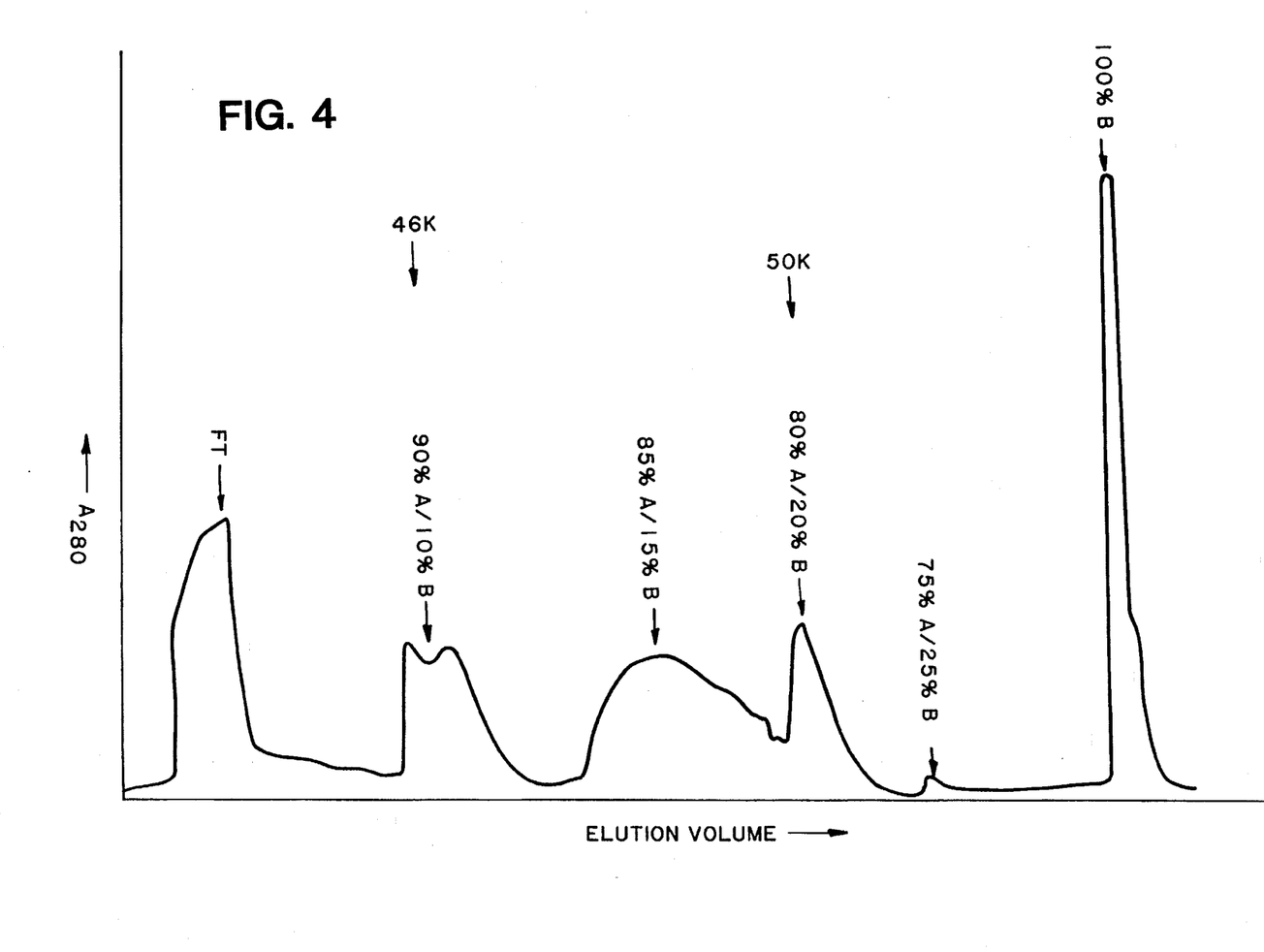
FIG. 4 illustrates purification of 46K and 50K proteins by hydrophobic interaction chromatography from a butyl fractogel column.

In order to separate the 50K from the 46K proteins, the flow through pool from the anion exchange column was adjusted to 30% ammonium sulfate concentration and then applied to a hydrophobic column of butyl fractogel (Toyohaus) previously equilibrated in 20 mM Tris, pH 7.0, containing 30% ammonium sulfate. Stepwise elution was then performed on the column by decreasing the ammonium sulfate concentration by 3% increments, down to a concentration of 21% ammonium sulfate in the Tris buffer. The column was then washed with 20 mM Tris/HCl, pH 7.4. The flow rate for this column was 1.0 ml/min. The profile obtained by this elution can be seen in FIG. 4. The 46K protein eluted at 27% ammonium sulfate concentration and the 50K protein eluted at 24% ammonium sulfate concentration. Both of these antigens were nearly homogeneous after this final step. Each pool from the column was dialyzed against 0.1M ammonium acetate buffer, pH 7.0, and then analyzed by SDS-PAGE and Western blot analysis. The 36K and 32K proteins of CTAA 28A32 were nearly homogeneous after the anion exchange column and did not need to be further purified.

Criteria of Purity

Figure 5:
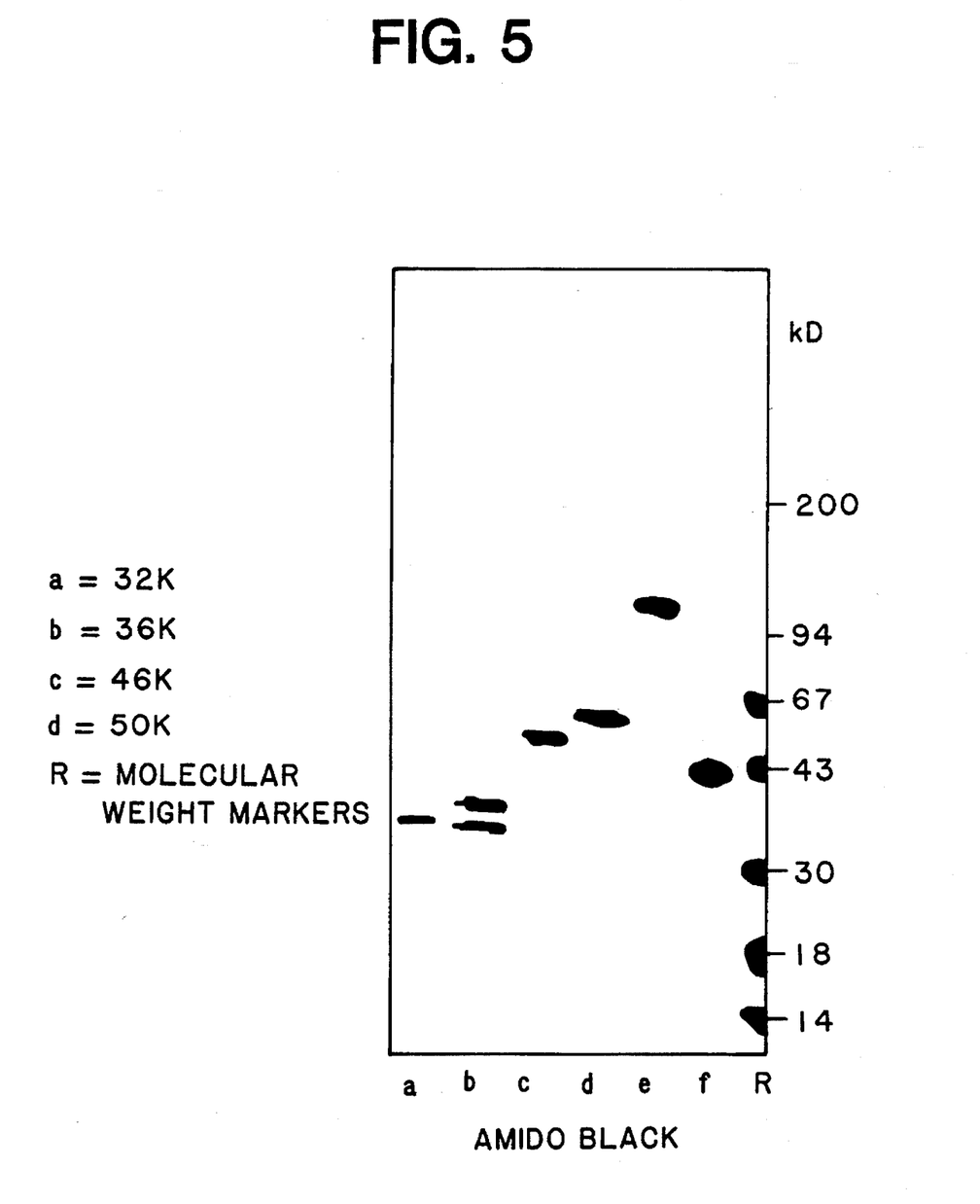

In order to assess the purity of the isolated proteins of CTAA 28A32, SDS polyacrylamide gel electrophoresis was performed for each protein. As can be seen in FIG. 5, the proteins seem to be nearly homogenous by this criterion.

Figure 6A:
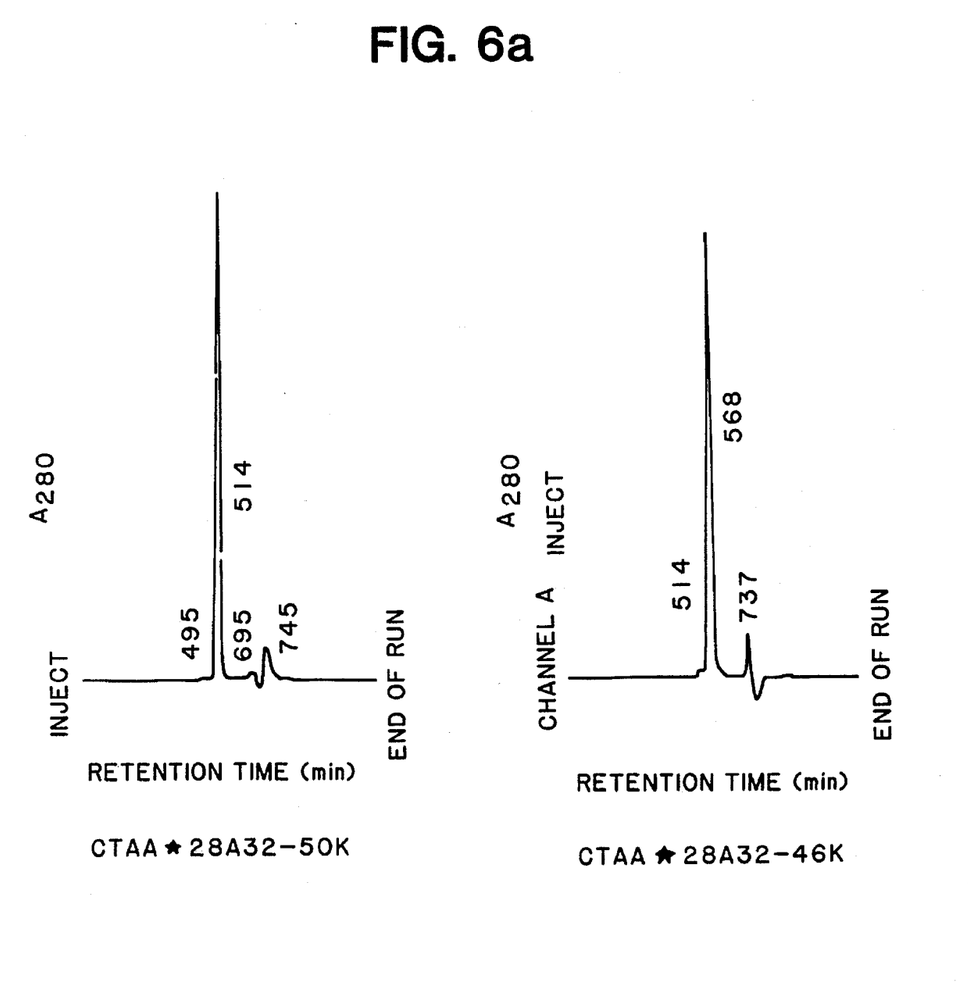
Figure 6B:
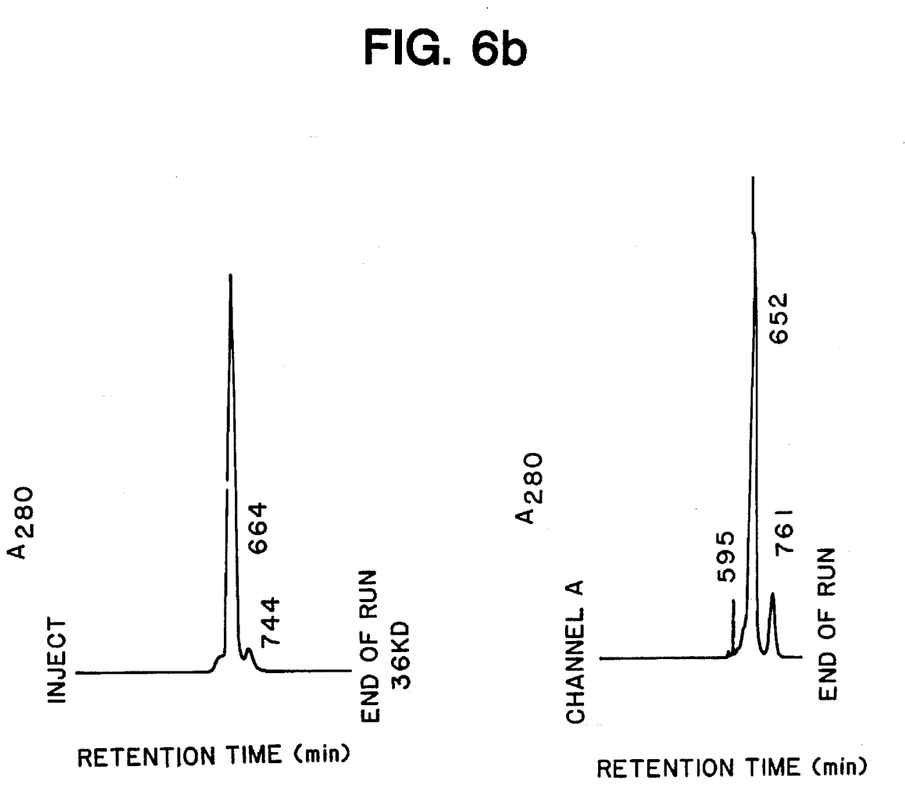

Purity of the native, non-denatured proteins was assessed by size exclusion high performance liquid chromatography (HPLC). As illustrated in FIG. 6, all proteins appear to be greater than 95% pure using this method.

Amino Acid Analysis

An amino acid analysis was performed using a Waters Pico-Tag method. The method involves hydrolysis of the protein under vacuum followed by derivatization of the resulting amino acids using phenylisothiocyanate. The derivatized amino acids were then separated and quantitated using reverse phase high performance liquid chromatography.

Each purified protein was subjected to hydrolysis followed by derivitization with phenylisothiocyanate and separation by reverse phase HPLC. The results of this analysis are reported in Table 4. The values are expressed as the number of residues of each amino acid per mole of protein. Each of the values represents an average of at least four separate determinations. As can be seen from this Table, each of the proteins differs from each other in amino acid composition.

Protein Sequence Analysis

Proteins were sequenced from the N-terminal portions of the molecule using an automated gas phase protein sequencer (Applied Biosystems, Inc.) based on the Edman degradation method. For those proteins that had a blockage of the N-terminal amino acid, thus preventing protein sequencing at this position, cleavage of the protein and isolation of peptides was performed. Standard methodology involved cleavage using cyanogen bromide or proteolytic enzymes followed by separation of the generated peptides by reverse phase high performance liquid chromatography. Individual peptides isolated in this way were subjected to N-terminal protein sequencing as described above.

Initial attempts to obtain sequence data for each of the proteins was unsuccessful except for the 36K protein, which was not blocked. The N-terminal amino acids of the 50K, 46K and 32K proteins were blocked and, thus, were not able to be sequenced at this position. In order to obtain protein sequence information about the blocked proteins, it was decided to fragment each purified protein and analyze the fragments for protein sequence information.

The 50K and 46K proteins were fragmented by cyanogen bromide cleavage, which has a specificity for cleavage at the carboxyl terminal portion of methionine residues within the protein. The 32K protein was fragmented by enzymatic digestion with Lys C, which has a specificity for carboxyl terminal cleavage of lysine residues within the protein. The peptides resulting from protein cleavage were separated by reverse phase high performance liquid chromatography. The peptide maps comparing each of these antigens using the same cleavage methods indicated different peptide maps for each protein. The fragment obtained by cleavage for each protein that represented the most predominant and reproducibly isolatable fragment was used to generate protein sequence information about a particular protein.

Figure 7:
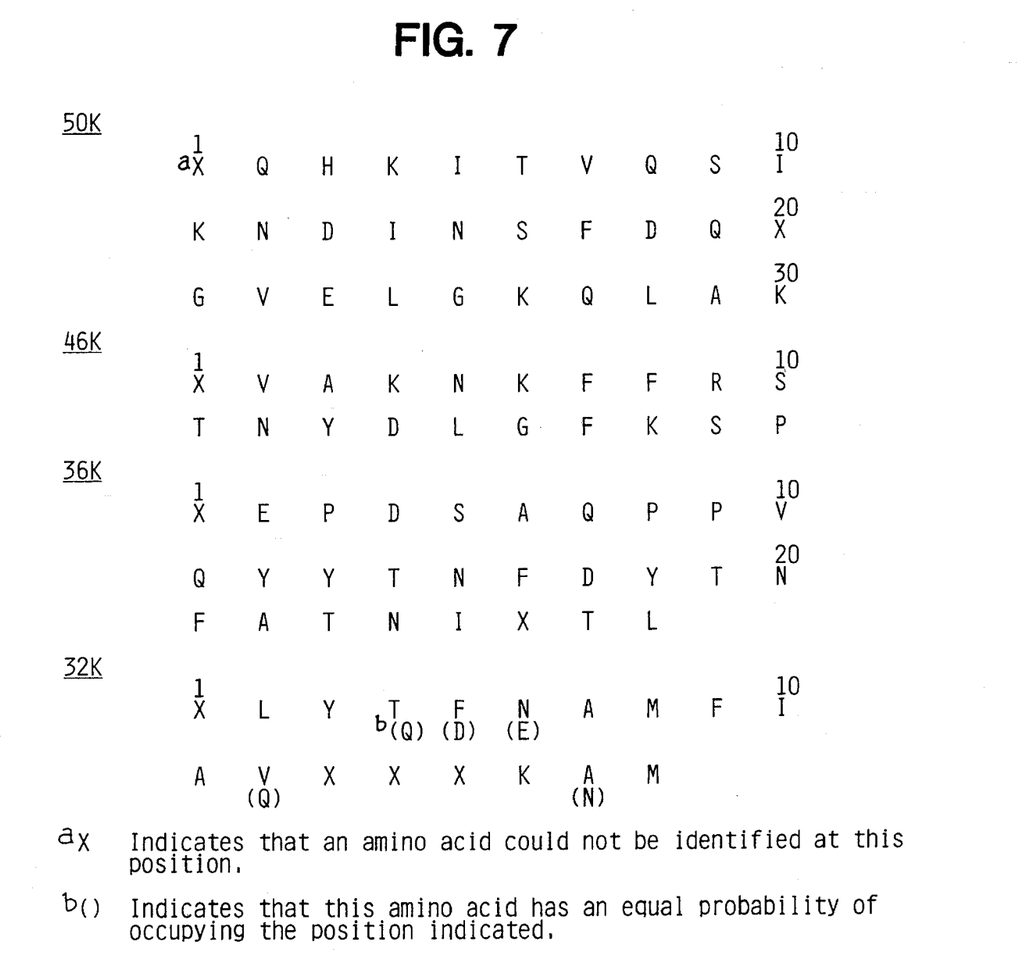
FIG. 7 provides protein sequence data for each of the antigens.

The data reported in FIG. 7 shows protein sequence information for the 50K, 46K, 36K and 32K proteins of CTAA 28A32. When these sequences were checked against existing protein databases, no significant homologies were found with known proteins except for the 46K protein, which had homology with human α enolase. This homology was approximately 75% to 80% and may indicate that this protein represents an altered form of α enolase produced in tumor cells. No other protein possess significant homologies with any other sequences listed in the protein database.

Human T-Cell Reactivity to CTAA 28A32
Generation and Analysis of Human T-Cell Clones Human T-cell clones were isolated from the tumor infiltrating lymphocytes of human colon carcinoma from five different individuals and tested for blastogenic responses to isolated pure CTAA 28A32 proteins. T-cells were cloned by plating collagenase dissociated human colon tumor cells by limiting dilution in 96 well plates containing $10^4$ autologous x-irradiated tumor cells as stimulators in a basal medium of RPMI-1640 supplemented with 10 units interleukin-2 (IL-2)/ml, 20% human AB serum, L-glutamine, sodium pyruvate, non-essential amino acids, HEPES buffer, penicillin, streptomycin, gentamicin and fungizone. T-cell clones were expanded in the same medium and stimulated every 7 to 14 days with autologous tumor to maintain their anti-tumor reactivity and specificity.

T-cell subset analysis was performed by flow cytometric analysis of cells labelled with fluorescein conjugated murine monoclonal antibodies to CD4 (T-helper) and CD8 (T cytotoxic) cell surface markers. Blastogenic responses of CD4 positive T-cell clones were determined using a microtiter assay where $10^5$ cloned T-cells were incubated in each well of 96-well microtiter plates with $5 \times 10^5$ autologous Epstein Barr virus transformed B cells (for antigen presentation), 10 μg/ml of test or control antigen immobilized on nitrocellulose in the growth medium reported above with the addition of one unit IL-2/ml, for six days at 37° C. Cells were pulsed with 1.0 μCi [$^3$H]-methyl thymidine for 18 hours, harvested onto fiberglass filters and counted in a scintillation counter to determine the amount of [$^3$H] incorporated, a measure of cell growth in response to specific stimulation by antigen. A stimulation index (SI) was calculated by dividing the counts per minute (CPM) of cells treated with test antigen by the CPM of cells treated with control antigen. A SI above 2.0 was considered significant.

The majority of the clones isolated were of the T-helper (CD4) phenotype. When assessed for reactivity to CTAA 28A32 proteins, clones from two different individuals (WOR and KEH) responded to the 46K protein (Table 6). Two different clones, #15 and #16, from WOR, and one clone, #11, from KEH proliferated in response to the 46K protein but none of the other CTAA 28A32 proteins. The 46K protein is not a general T-cell stimulator, as clones from other individuals did not respond (see Table 5, ROBC63).

Because T-cell immunity is a key factor in tumor regression in man and animals, the T-cell responses from tumor bearing individuals to the tumor associated antigens may be indicative of the relevancy of these antigens as a vaccine for human colon cancer. The fact that negative responses were obtained for 50K, 36K and 32K proteins of CTAA 28A32 is not significant since a large number of clones would have to be tested in order to determine that these proteins were not suitable vaccine candidates. The reactivity of the 46K protein is significant since three separate reactive T-cell clones were identified indicating that this antigen may be relevant for use as a vaccine.

TABLE 1

REACTIVITY OF MCA 28A32 ANTIBODY
WITH AIR-DRIED COLON
TUMOR CELL LINES AND XENOGRAFT CELLS

| Cell Lines | Antibody Concentration | Reactivity |
|---|---|---|
| HT-29 | 0.3 μg/slide | 2+ |
| SW-1463 | 0.3 μg/slide | 2+ |
| SW-948 | 0.3 μg/slide | 4+ |
| SW-403 | 0.3 μg/slide | 3+ |
| LS-174 | 0.3 μg/slide | 3+ |
| LoVo | 0.3 μg/slide | 3+ |
| WiDr | 0.3 μg/slide | 1+ |
| ATK Xenograft | 17 ng/slide | 1+ |
| JEF Xenograft | 85 ng/slide | 1+ |
| THO Xenograft | 17 ng/slide | 1+ |
| BLU Xenograft | 17 ng/slide | 1+ |

TABLE 2

SUMMARY OF BIOTINYLATED 28A32 REACTIVITY ON FORMALIN-FIXED COLON TUMOR AND NORMAL COLON TISSUE

| Antibodies | Dilution | IgM μg/ml | Patient #1 | | Patient #2 | | Patient #3 | | Patient #4 | |
|---|---|---|---|---|---|---|---|---|---|---|
| | | | B-0133 Colon (T) | B-0134 Colon (N) | B-0477 Colon (T) | B-0475B-0550 Colon (N) | B-0549 Colon (T) | B-0639 Colon (N) | B-0646 Colon (T) | Colon (N) |
| 28A32/B | 1:10 | 40 | 4 | 1 | 0 | 0 | 3 | 1 | 1 | 0 |
| | 1:20 | 20 | 3 | 0 | 0 | 0 | 2 | 0 | 0 | 0 |
| | 1:40 | 10 | 1 | 0 | 0 | 0 | 1 | 0 | 0 | 0 |
| IgM/B (Control) | 1:5 | 80 | — | — | — | — | 0 | 0 | — | — |
| | 1:10 | 40 | 0 | 0 | 0 | 0 | 0 | 0 | 0 | 0 |
| | 1:20 | 20 | 0 | 0 | 0 | 0 | 0 | 0 | 0 | 0 |
| | 1:40 | 10 | 0 | 0 | 0 | 0 | — | — | 0 | 0 |

| Antibodies | Dilution | IgM μg/ml | Patient #5 | | Patient #6 | | Patient #7 | |
|---|---|---|---|---|---|---|---|---|
| | | | B-0660 Colon (T) | B-0654 Colon (N) | B-0685 Colon (T) | B-0686 Colon (N) | B-0689 Colon (T) | B-0696 Colon (N) |
| 28A32/3 | 1:10 | 40 | 2 | 0 | 3 | 1 | 2 | 1 |
| | 1:20 | 40 | 1 | 0 | 1 | 0 | 1 | — |
| | 1:40 | 10 | 0 | 0 | 0 | 0 | 1 | 0 |
| IgM/B (Control) | 1:5 | 80 | — | — | — | — | — | — |
| | 1:10 | 40 | 0 | 0 | 0 | 0 | 0 | 0 |

TABLE 2-continued

SUMMARY OF BIOTINYLATED 28A32 REACTIVITY ON FORMALIN-FIXED
COLON TUMOR AND NORMAL COLON TISSUE

|  |  |  |  |  |  |  |  |
|---|---|---|---|---|---|---|---|
| 1:20 | 20 | 0 | 0 | — | — | 0 | 0 |
| 1:40 | 10 | 0 | 0 | — | — | 0 | 0 |

Key:
— = Not Tested

TABLE 3

SUMMARY OF BIOTINYLATED 28A32 REACTIVITY ON FORMALIN-FIXED
NORMAL TISSUE - NORMAL TISSUE

| Antibodies | Dilution | IgM µg/ml | B-0161 Breast | B-0178 Breast | B-0761 Esophagus | B-0780 Esophagus | B-0342 Esophagus | B-0197 Stomach | Stomach | B-0243 G Blad |
|---|---|---|---|---|---|---|---|---|---|---|
| 28A32/B | 1:10 | 40 | 0 | 0 | 0 | $2^{(1)}$ |  | 0 | 0 | $1^{(2)}$ |
|  | 1:20 | 20 | 0 | 0 | 0 | 1 |  | 0 | 0 | $1^{(2)}$ |
|  | 1:40 | 10 | 0 | 0 | 0 | 0 |  | 0 | 0 | 0 |
|  | 1:50 | 8 | — | — | — | — |  | — | — | — |
|  | 1:250 | 1.6 | — | — | — | — |  | — | — | — |
| Human | 1:5 | 80 | — | — | 0 | 0 |  | — | — | — |
| IgM/B | 1:10 | 40 | 0 | 0 | 0 | 0 |  | $1^{(12)}$ | 0 | 0 |
|  | 1:20 | 20 | 0 | 0 | — | — |  | 0 | 0 | — |
|  | 1:40 | 10 | 0 | 0 | — | — |  | 0 | 0 | — |

| Antibodies | Dilution | IgM µg/ml | B-0579 Kidney | B-0599 Kidney | B-0270 Liver | B-0503 Liver | B-0165 Lung | B-0257 Lung | B-0679 Ovary | B-0306 Skin | B-0680 Teste |
|---|---|---|---|---|---|---|---|---|---|---|---|
| 28A32/B | 1:10 | 40 | 2 | $2^{(3)}$ | 0 | $1^{(4)}$ | 0 | 0 | 0 | $1^{(5)}$ | $1^{(6)}$ |
|  | 1:20 | 20 | 1 | $1^{(3)}$ | 0 | 0 | 0 | 0 | 0 | $1^{(5)}$ | 0 |
|  | 1:40 | 10 | — | $1^{(3)}$ | 0 | 0 | 0 | 0 | — | $0^{(5)}$ | 0 |
|  | 1:50 | 8 | — | — | — | — | — | — | — | — | — |
|  | 1:250 | 1.6 | — | — | — | — | — | — | — | — | — |
| Human | 1:5 | 80 | — | — | — | — | — | — | — | — | — |
| IgM/B | 1:10 | 40 | 0 | 0 | 0 | 0 | 0 | 0 | 0 | 0 | 0 |
|  | 1:20 | 20 | 0 | 0 | 0 | 0 | 0 | 0 | — | 0 | 0 |
|  | 1:40 | 10 | 0 | 0 | 0 | 0 | 0 | 0 | — | 0 | 0 |

Key:
— = Not Tested
[1] Squamous epithelium and underlying muscle
[2] Epithelium and connective tissue
[3] Epithelium of tubules
[4] Epithelium of ducts
[5] Epidermis
[6] Interstitial cells

TABLE 4

AMINO ACID ANALYSIS OF CTAA 28A32

| Amino Acid | Antigen | | | |
|---|---|---|---|---|
|  | 50K | 46K | 36K | 32K |
| D, N | $^a$40 | 36 | 25 | 26 |
| E, Q | 53 | 37 | 32 | 34 |
| S | 28 | 25 | 23 | 25 |
| G | 41 | 30 | 18 | 29 |
| H | 13 | 4 | 3 | 3 |
| R | 23 | 21 | 19 | 17 |
| T | 31 | 21 | 18 | 16 |
| A | 34 | 31 | 26 | 21 |
| P | 16 | 13 | 7 | 7 |
| Y | 13 | 16 | 17 | 11 |
| V | 15 | 18 | 14 | 12 |
| M | 4 | 6 | 6 | 5 |
| I | 15 | 17 | 15 | 13 |
| L | 39 | 33 | 25 | 23 |
| F | 13 | 14 | 5 | 8 |
| K | 41 | 22 | 28 | 18 |
| W | 3 | 2 | 1 | 2 |
| C | 4 | 3 | 2 | 2 |

$^a$Expressed as the total number of amino acid residues per mole of antigen.

TABLE 5

HUMAN T-CELL CLONES BLASTOGENIC RESPONSES TO TUMOR AMTIGENS[a]

| ANTIGEN | CPM (SI)[b] | | | |
|---|---|---|---|---|
| | WOR C15 | WOR C16 | KEH CII | ROB C63 |
| Media Control | 444 | 454 | 11,705 | 1,827 |
| Nitrocellulose Control | 418 | 446 | 11,527 | 2,225 |
| CTA #2 p50 | 408 (1.0) | 319 (0.7) | 28,604 (2.2) | 3,749 (1.5) |
| CTA #2 p46 | 1,328 (3.2) | 1,236 (2.8) | 36,695 (2.9) | 4,073 (1.7) |
| CTA #2 p36 | 430 (1.0) | 436 (1.0) | 17,907 (1.4) | 2,796 (1.1) |
| CTA #2 p32 | 522 (1.2) | 581 (1.3) | 21,391 (1.7) | 2,693 (1.1) |

[b]C.P.M. is mean counts per minute of triplicate measurements; S.I. is the stimulation index determined by dividing the C.P.M. of cells in the presence of test antigen by the C.P.M. of cells in the presence of the nitrocellulose control.
[a]Cloned T-cells at $10^5$ cells/well from patient WOR, KEH and ROB were incubated six days with $5 \times 10^5 \times$ irradiated autologous EBV-transformed B-cells, 1U IL-2/ml and 10 µg nitrocellulose immobilized test antigen/ml then pulsed with 1 µCi [$^3$H]-TdR, harvested and counted.

REFERENCES

1. Silverberg, E., *CA* (1983) 33:9–25.
2. Goligher, J. C., Surgery of the Anus, Rectum and Colon, 4th ed., London: Baillere Tindall (1980) 47–471.
3. Hoover, H. C., Jr. et al. *Biologic Therapy of Cancer Principles and Practices.* (1990) In press. J. P. Lippincott Co.
4. Hoover, H. C., Jr., et al. *Cancer* (1985) 55:1236–1243.
5. Gold, P. and Freedman, S. O., *J. Exp. Med.* (1965) 122:467–481.
6. Yeoman, L. C. et al., Human Colon Tumor Antigens. In: H. Busch and L. C. Yeoman (eds.), Vol. 19, 231–271, New York: Academic Press, Inc. (1982).
7. Magnani, J. L. et al., *Cancer Res.* (1983) 43:5489–5492.
8. Artigas, C. et al., *Cancer Res.* (1986) 45:1874–1881.
9. Blaszczyk, M. et al., *Cancer Res.* (1984) 44:245–253.
10. Ross, A. H., et al., *Biochem. Biophys. Res. Comm.* (1986) 135:297–303.
11. Haspel, M. V. et al., *Cancer Res.* (1985) 45:3951–3961.

We claim:

1. A substantially purified human tumor cell antigen that elicits a cellular immune response in humans comprising an epitope immunoreactive with human monoclonal antibody 28A32, said antibody having ATCC accession number HB9380, found on a tumor associated antigen shared by colon carcinoma cell lines HT-29, SW1463, SW948, SW403 and LoVo, having ATCC accession numbers HB 38, CCL 234, CCL 237, CCL 230 and CCL 229.

2. The substantially purified human tumor cell antigen of claim 1, having a molecular weight of 50Kd, 46Kd, 36Kd or 32Kd determined by SDS polyacrylamide gel electrophoresis that are immunoreactive with the human monoclonal antibody 28A32.

3. A substantially purified tumor cell antigen according to claim 2 that elicits a cellular immune response in humans having a molecular weight of about 46Kd, 36Kd or 32Kd determined by SDS polyacrylamide gel electrophoresis.

4. The substantially purified tumor cell antigen of claim 3, having a molecular weight of about 32Kd determined by SDS polyacrylamide gel electrophoresis.

5. A vaccine comprising an immunogenically effective amount of at least one antigen defined by claim 3.

* * * * *